US011497558B2

(12) United States Patent
Ferrara et al.

(10) Patent No.: US 11,497,558 B2
(45) Date of Patent: Nov. 15, 2022

(54) METHOD FOR DETERMINING THE POSITIONING IN DEPLOYED POSITION OF AN IMPLANTABLE MEDICAL DEVICE AFTER EXPANSION IN A VASCULAR STRUCTURE

(71) Applicant: SIM&CURE, Montpellier (FR)

(72) Inventors: Riccardo Ferrara, Montpellier (FR); Mathieu Sanchez, Cournonterral (FR); Vincent Costalat, Saint-Gely-du-Fesc (FR); Dominique Ambard, Aniane (FR); Christophe Chnafa, Montpellier (FR); Julien Siguenza, Montpellier (FR)

(73) Assignee: SIM&CURE, Montpellier (FR)

( * ) Notice: Subject to any disclaimer, the term of this patent is extended or adjusted under 35 U.S.C. 154(b) by 342 days.

(21) Appl. No.: 16/772,713

(22) PCT Filed: Dec. 17, 2018

(86) PCT No.: PCT/FR2018/053343
§ 371 (c)(1),
(2) Date: Jun. 12, 2020

(87) PCT Pub. No.: WO2019/122665
PCT Pub. Date: Jun. 27, 2019

(65) Prior Publication Data
US 2020/0323592 A1    Oct. 15, 2020

(30) Foreign Application Priority Data
Dec. 19, 2017 (FR) ...................................... 1762490

(51) Int. Cl.
*G06K 9/00* (2022.01)
*A61B 34/10* (2016.01)
(Continued)

(52) U.S. Cl.
CPC ............. *A61B 34/10* (2016.02); *G16H 20/30* (2018.01); *G16H 50/50* (2018.01);
(Continued)

(58) Field of Classification Search
CPC ......... G06T 7/0012; G06T 2207/10081; G06T 2207/10088; G06T 2207/10108;
(Continued)

(56) References Cited

U.S. PATENT DOCUMENTS

2003/0195411 A1    10/2003  Sureda et al.
2010/0195879 A1*    8/2010  Bernhardt ............... G06T 19/00
                                                                        382/128
(Continued)

FOREIGN PATENT DOCUMENTS

DE    102006058908 A1    4/2008
EP        3025638 A1    6/2016

OTHER PUBLICATIONS

LaDisa, Alterations in regional vascular geometry produced by theoretical stent implantation influence distributions of wall shear stress: analysis of a curved coronary artery using 3D computational fluid dynamics modeling, Jun. 2006, BioMed Central (Year: 2006).*
(Continued)

*Primary Examiner* — Alex Kok S Liew
(74) *Attorney, Agent, or Firm* — Womble Bond Dickinson (US) LLP

(57) ABSTRACT

A method for determining the positioning in deployed position of an expandable medical device type implant, including, from a three-dimensional image of a region of interest including the vascular structure, the following steps: determination of a centreline of the vascular structure, positioning of the IMD according to an initial position, around the centreline, simulation of the final position of the IMD after deployment, as a function of the stresses exerted by the walls of the vascular structure on the IMD, the determination of the centreline consisting in placing points so as to minimise a travel time of fluid along said points between an input point and an output point, the simulation of the final position of the IMD taking account of a level of
(Continued)

longitudinal push-pull intended to be applied to the IMD during its implantation.

15 Claims, 11 Drawing Sheets

(51) Int. Cl.
*G16H 20/30* (2018.01)
*G16H 50/50* (2018.01)
*A61B 17/12* (2006.01)
*A61F 2/91* (2013.01)
*A61F 2/06* (2013.01)

(52) U.S. Cl.
CPC ... *A61B 17/12113* (2013.01); *A61B 17/12168* (2013.01); *A61B 2034/104* (2016.02); *A61B 2034/105* (2016.02); *A61F 2/91* (2013.01); *A61F 2002/068* (2013.01)

(58) Field of Classification Search
CPC . G06T 2207/30104; G06T 2207/10104; G06T 2207/30048; G06T 2207/10072; G06T 2210/41; G06T 7/11; G06T 2200/04; G06T 11/001; G06T 17/00; G06T 17/20; G06T 7/0014; G06T 7/12; G06T 11/60; G06T 7/20; G06T 7/62; G06T 2211/404; G06T 11/00; G06T 11/008
See application file for complete search history.

(56) References Cited

U.S. PATENT DOCUMENTS

| | | | |
|---|---|---|---|
| 2013/0243294 A1* | 9/2013 | Ralovich | G06T 7/0012 382/131 |
| 2016/0232659 A1† | 8/2016 | Larrabide | |
| 2020/0279643 A1* | 9/2020 | Srivastava | G06T 7/62 |

OTHER PUBLICATIONS

International Preliminary Report on Patentability received for PCT Patent Application No. PCT/FR2018/053343, dated Jul. 2, 2020, 15 pages (8 pages of English Translation and 7 pages of Original Document).
International Search Report and Written Opinion received for PCT Patent Application No. PCT/FR2018/053343, dated Apr. 29, 2019, 18 pages (8 pages of English Translation and 10 pages of Original Document).
Jin et al., "A New Approach of Arc Skeletonization for Tree-like Objects Using Minimum Cost Path", 22nd International Conference on Pattern Recognition, IEEE Computer Society, Aug. 24, 2014, pp. 942-947.
Lorensen et al., "Marching Cube: A high resolution 3D surface construction algorithm", Computer Graphics, Computer Graphics, vol. 21, No. 4, Jul. 1987, pp. 163-169.
Preliminary Research Report received for French Application No. 1762490, dated Sep. 26, 2018, 2 pages (1 page of French Translation Cover Sheet and 1 page of original document).
Bianchi, M. et al. "Effect of Balloon-Expandable Transcatheter Aortic Valve Replacement Positioning: A Patient-Specific Numerical Model." E292-E304, (2016), Artificial Organs vol. 40, 12(2016):doi:10.1111/aor.12806.†
Ma, D. et al. "High Fidelity Virtual Stenting (HiFiVS) for Intracranial Aneurysm Flow Diversion: In Vitro and In Silico." entire article, (2013), Annals of Biomedical Engineering (Apr. 2013): doi:10.1007/s10439-013-0808-4.†
Antiga, L. "Patient-specific modeling of geometry and blood flow in large arteries." pp. 1-178, (2002), PhD. Thesis, Politecnico Di Milano Dipartimento Di Bioingegneria.†
Kerrien, E. et al. "Blood vessel modeling for interactive simulation of interventional neuroradiology procedures." pp. 685-698, (2017), Medical image analysis vol. 35 (2017): doi:10.1016/j.media.2916.10.003.†

\* cited by examiner
† cited by third party

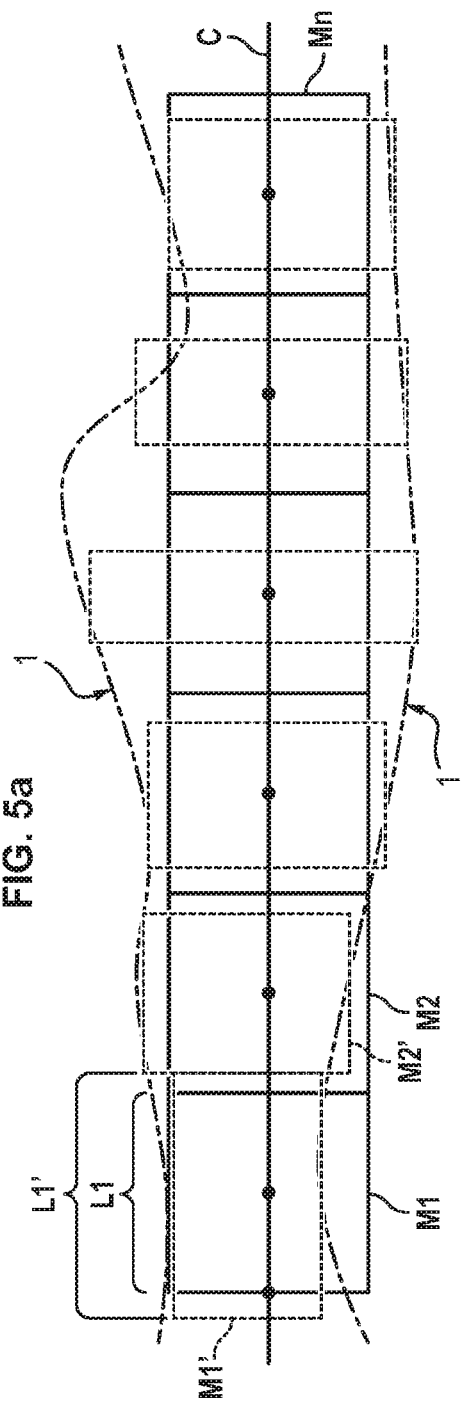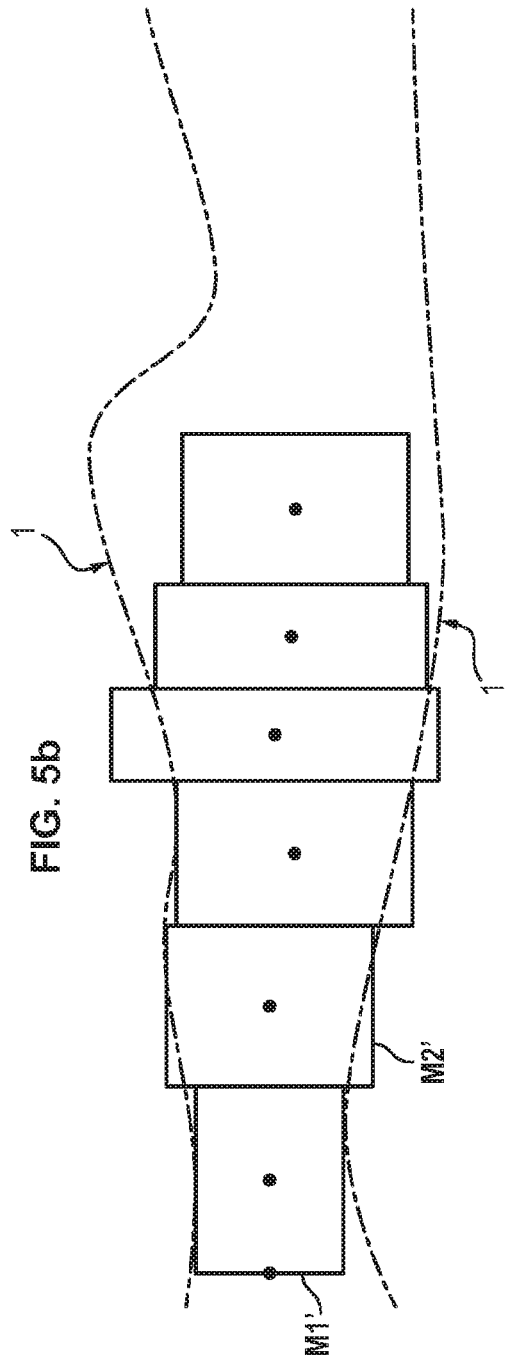

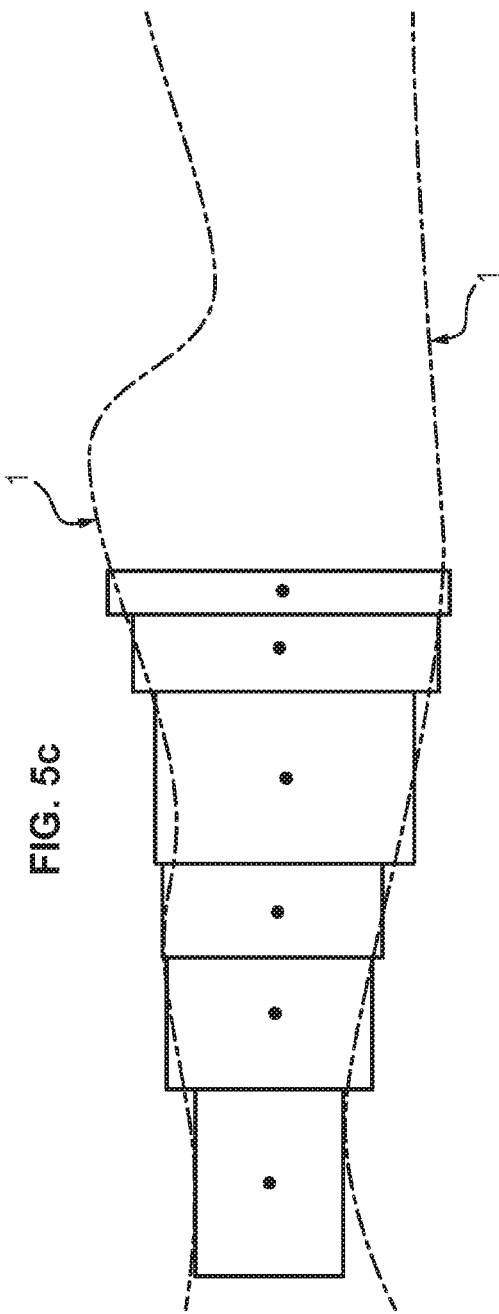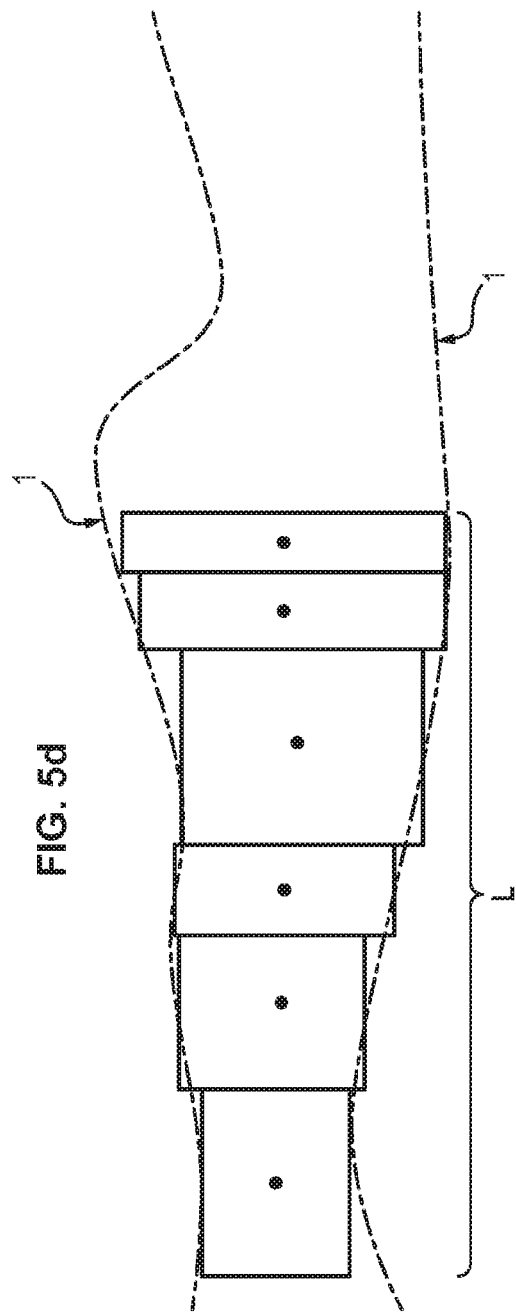

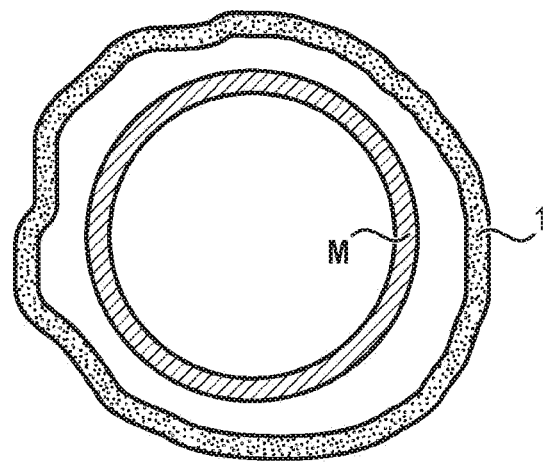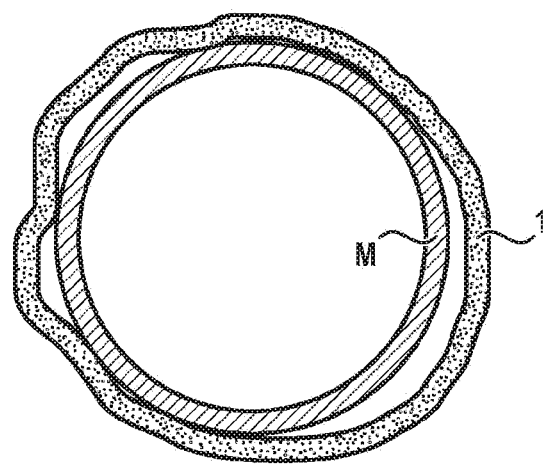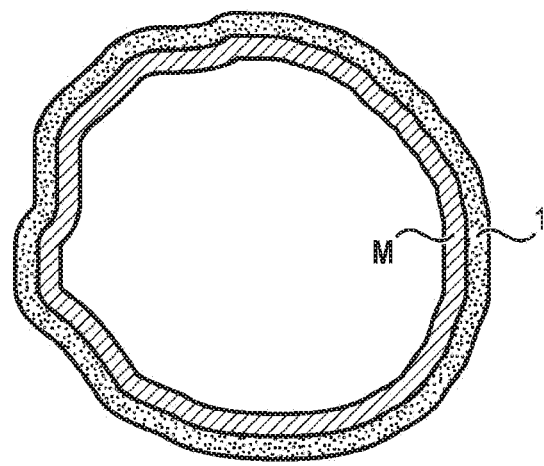
FIG. 6 ately, the invention makes it possible to offset the aforementioned drawbacks and...

METHOD FOR DETERMINING THE POSITIONING IN DEPLOYED POSITION OF AN IMPLANTABLE MEDICAL DEVICE AFTER EXPANSION IN A VASCULAR STRUCTURE

TECHNICAL FIELD OF THE INVENTION AND PRIOR ART

The present invention pertains to the field of digital simulation of vascular implants, before or during the implant operation.

More specifically, the invention relates to the prediction of the mechanical behaviour of an implantable medical device (or IMD), for which three-dimensional mapping of a vascular structure, such as an artery, suffering from a local pathology such as an aneurysm, is available before the insertion of said implant by endovascular route. This prediction is useful for the clinician for the choice of an optimal size and an optimal initial positioning of the device, or even the choice of an optimal model, during the intervention.

It is common practice to use an implant of expandable implantable medical device (IMD) type, such as a "stent", an "intrasaccular cage", or a "flow diverter", to treat for example an artery affected by an aneurysm. It is wished to avoid the expansion and the rupture of the aneurysm, and furthermore, to avoid that clots formed in the aneurysmal sac migrate and locally block an artery.

Such an implant may be inserted by percutaneous implantation. The implant may be conserved in a radially compressed state in a catheter, and deploy after positioning in a zone to treat. The IMD may be of cylindrical, spherical, ellipsoid shape or of tubular shape with variable radius around its axis of revolution.

It is important to predict, before the implantation, the deployed position adopted by the implant. For example, in the case of a "flow diverter", the implant may extend (with respect to its length at rest) along its longitudinal axis after the insertion of the implant. In the case of an intrasaccular or intraaneurysmal cage with variable geometry, the implant may extend longitudinally and radially around its axis of revolution after its deployment in the aneurysmal sac, such that the implant after expansion hugs the shape of the aneurysmal sac up to mechanical equilibrium. For the treatment of an aneurysm, the final length of the implant, its exact positioning, its diameter, its apposition against the walls of the artery are as many parameters of which the control is important. A device deploying over too long a length may cover an arterial bifurcation in an undesired manner. A device of too short length may treat in an insufficient manner the aneurysmal pathology. In addition, if the apposition of the device against the walls of the artery is unsatisfactory, there exists a risk of formation of a thrombus.

The planning of an implant insertion by endovascular route is generally carried out by means of two-dimensional or three-dimensional images of the artery. Until now, the choice of the IMD reference to be deployed has been based—at least—on local planar measurements (2D) carried out by the physician on the imaging of the patient. These measurements do not make it possible to predict, in a reliable manner, an apposition of the IMD or its final length once deployed.

In order to take into account the morphology of the vascular structure to estimate the final position of an endovascular implant after deployment, techniques based on the use of abacuses are known. The abacuses give a relationship between the length of the device after deployment and its diameter. Assuming that the expansion of the implant is limited by the minimum diameter of the vascular structure that surrounds it, it is possible to obtain an estimation of length after deployment. However, this technique presupposes a vascular structure having a constant circular section.

Thus, there exists a need for a method for determining the final position of an implant after deployment, and notably its radial expansion after deployment, which is very precise and reliable.

There exists an additional need for a model capable of giving an estimation of the apposition of the implant against the walls of the vascular structure.

GENERAL DESCRIPTION OF THE INVENTION

The invention makes it possible to offset the aforementioned drawbacks and proposes, according to a first aspect, a method for determining the positioning in deployed position of an expandable implantable medical device, or IMD, said medical device being intended to be deployed in a vascular structure, the method comprising, from a three-dimensional image of a region of interest comprising the vascular structure in which a point of positioning of the IMD within the vascular structure has been defined, the following steps:

determination of a centreline of the vascular structure, positioning of the IMD according to an initial position, around the centreline, simulation of the final position of the IMD after deployment, as a function of the stresses exerted by the walls of the vascular structure on the IMD, the determination of the centreline consisting in placing points at different longitudinal positions along the vascular structure, so as to minimise a travel time of fluid along said points between an input point in the vascular structure and an output point of the vascular structure, said points forming the centreline, and the simulation of the final position of the IMD being carried out as a function of a level of longitudinal push-pull intended to be applied to the IMD during its implantation.

The invention has multiple advantages.

The invention, which applies for the simulation of an implant in humans as well as in animals, improves the determination of the centreline, a three-dimensional image of the vascular structure being used to determine the points of the centreline. In addition, the use of a gradient descent algorithm makes it possible to obtain a centreline closer to physical reality. The centreline thus determined is more faithful to the actual longitudinal axis of the implant after deployment.

This centreline serves as basis for the correction of the position of the IMD, to determine a final position of the IMD, and notably its length after deployment.

The taking into account of a level of push-pull, during the correction of the position of the IMD, makes this correction more reliable since account is taken of the mechanical stress exerted during the insertion of the implant, which can go for example in the sense of a radial expansion of the implant. Cases where the implant locally adopts an equilibrium position different from a cylinder of revolution shape are then modelled. Indeed, for a non-zero level of push-pull, the radial force exerted by the implant brings closer together the walls of the implant and the surface of the vascular structure.

Additional and non-limiting characteristics of a method according to the first aspect of the invention are those defined in each of claims 2 to 12, taken alone or in any technically possible combinations thereof.

According to a second aspect, the invention relates to a computer programme product comprising code instructions for the execution of a method such as described above, when it is executed by processing means of a processing unit.

According to another aspect, the invention relates to a processing unit configured to obtain a three-dimensional image of a vascular structure acquired from an acquisition unit, and further configured to simulate a final position of an expandable IMD, by the implementation of a method such as described above.

GENERAL DESCRIPTION OF THE FIGURES

Other characteristics, aims and advantages of the invention will become clear from the description that follows, which is purely illustrative and non-limiting, accompanied by the appended drawings among which:

Figure 3A:
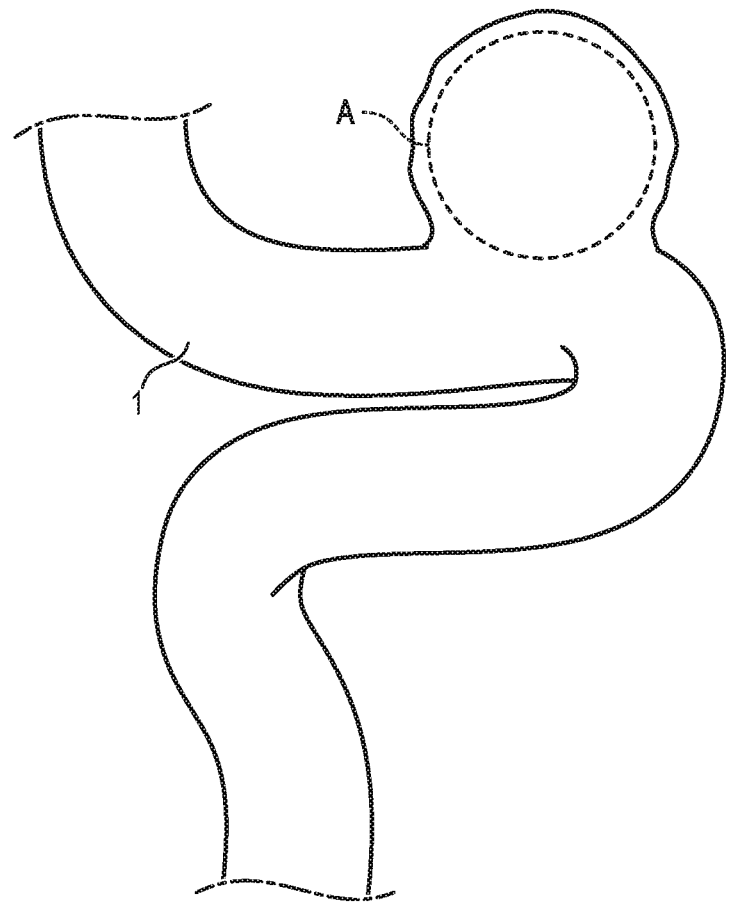
FIG. 3a is an angiography of the artery suffering from an aneurysm.
Figure 3B:
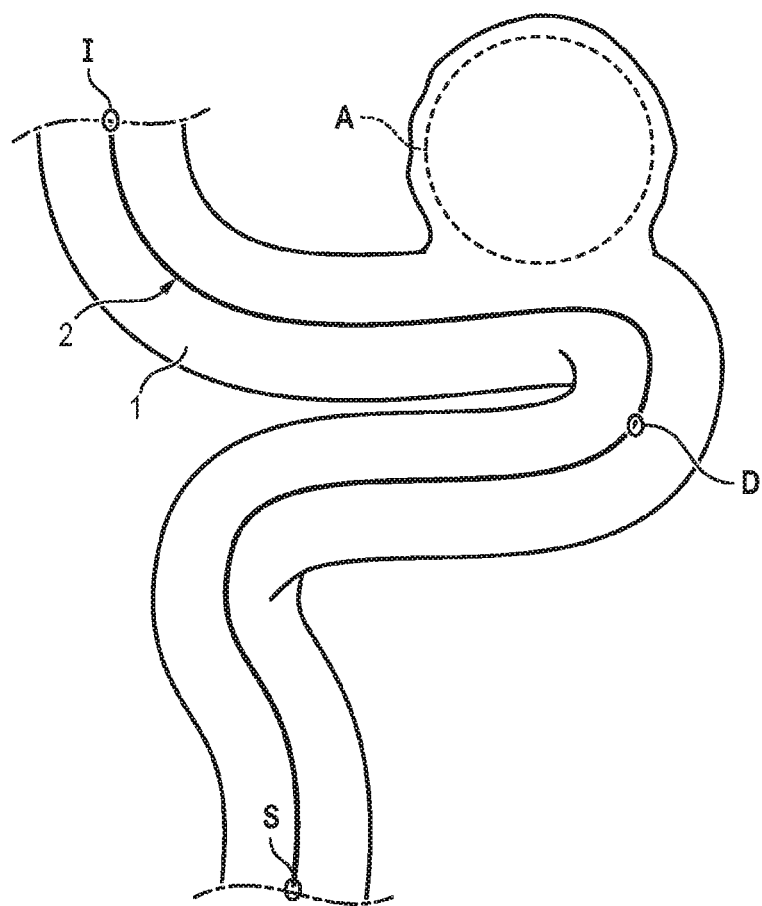
Figure 3C:
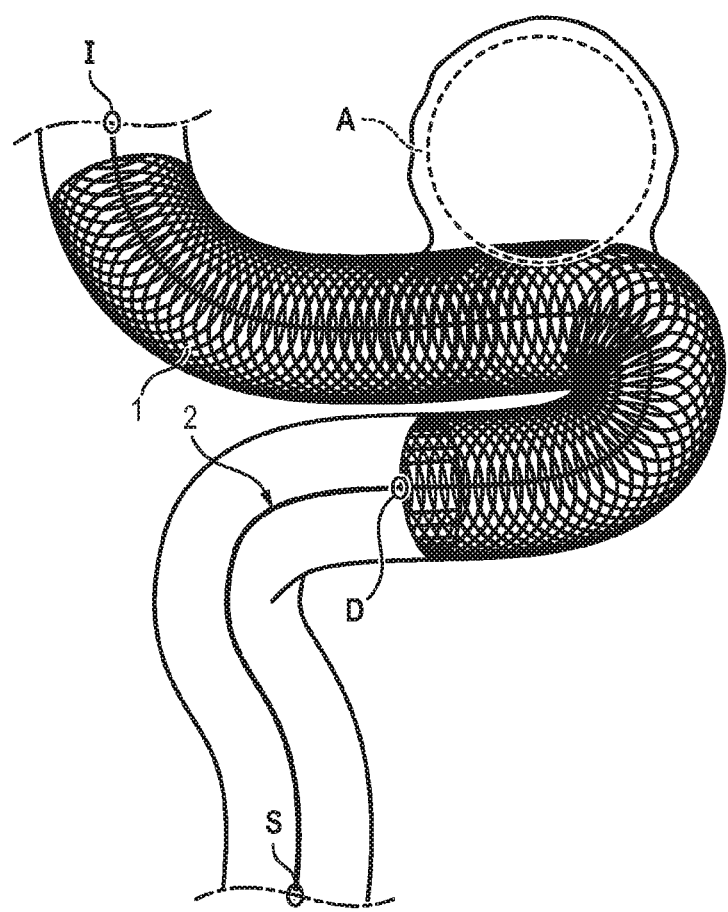
Figure 4A:
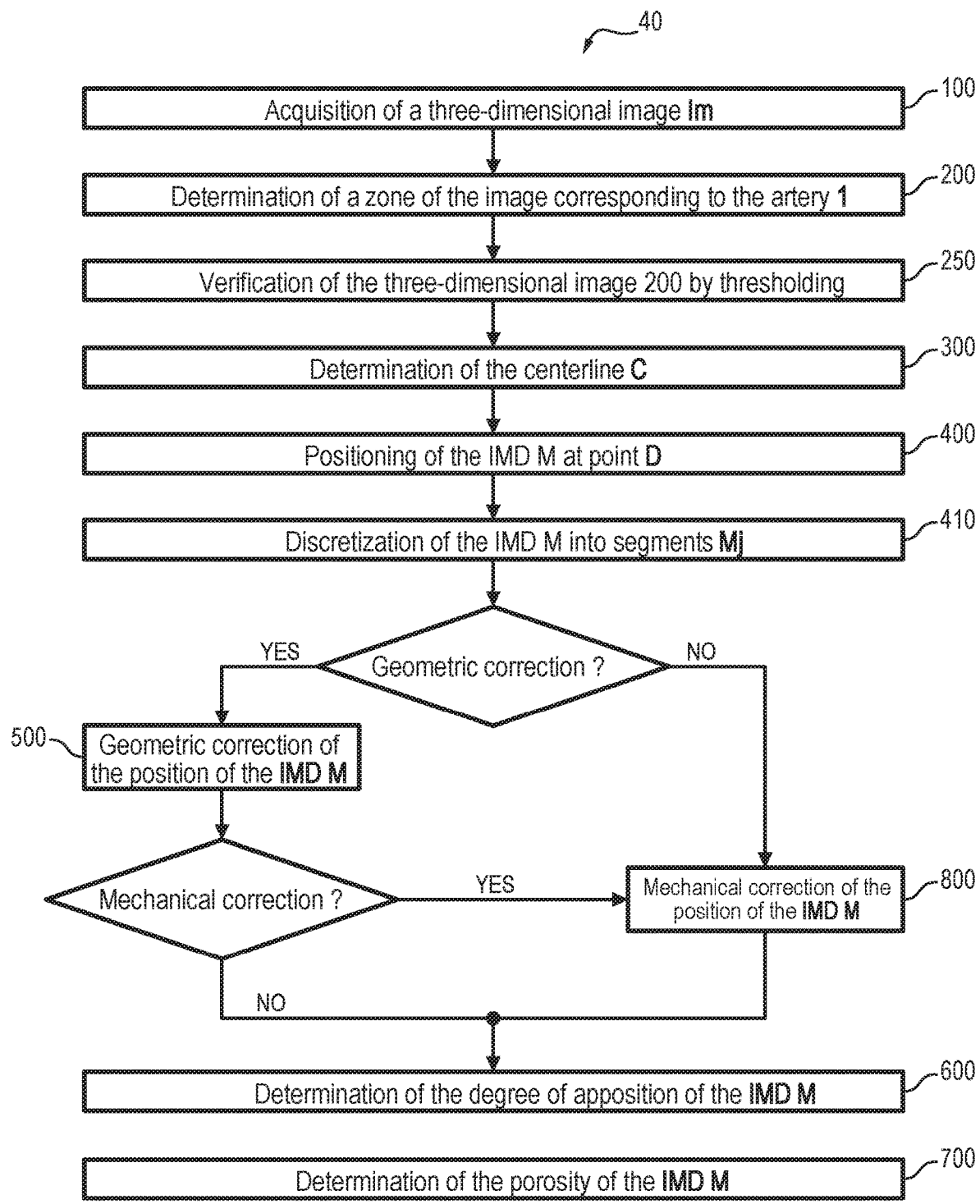
Figure 4B:
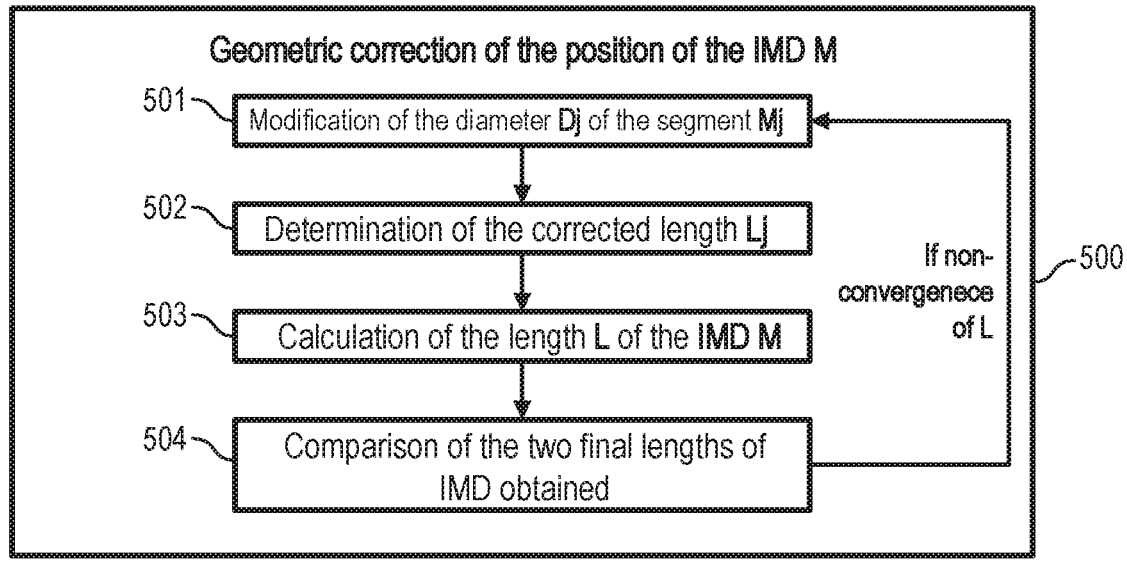
Figure 4C:
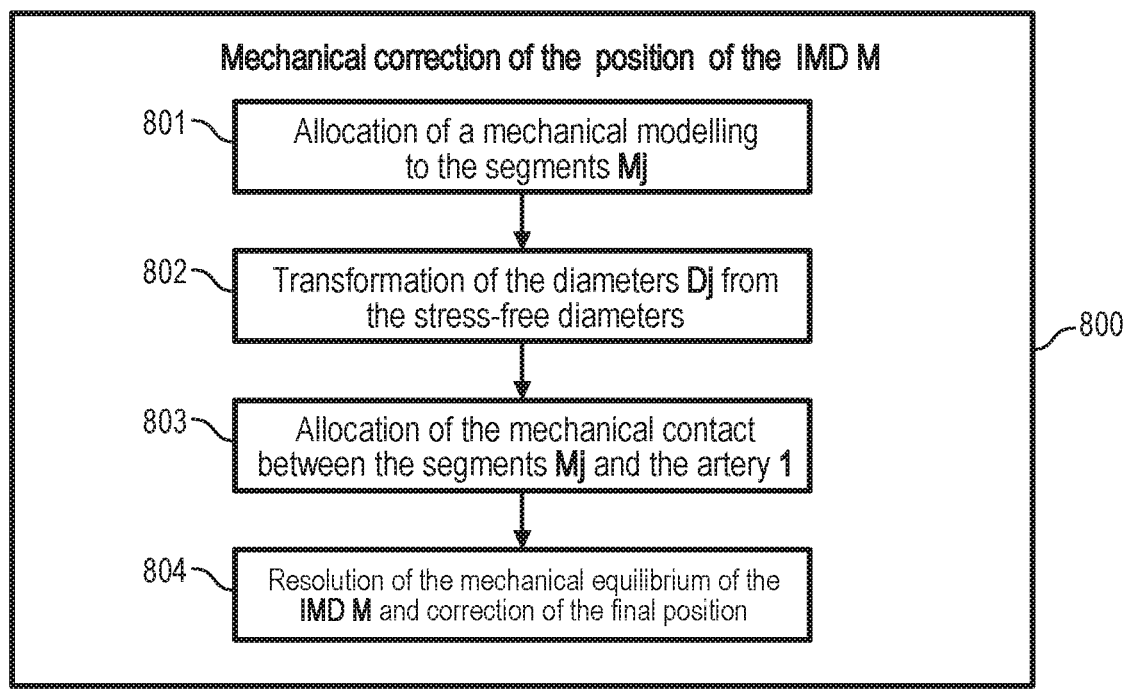
Figure 7:
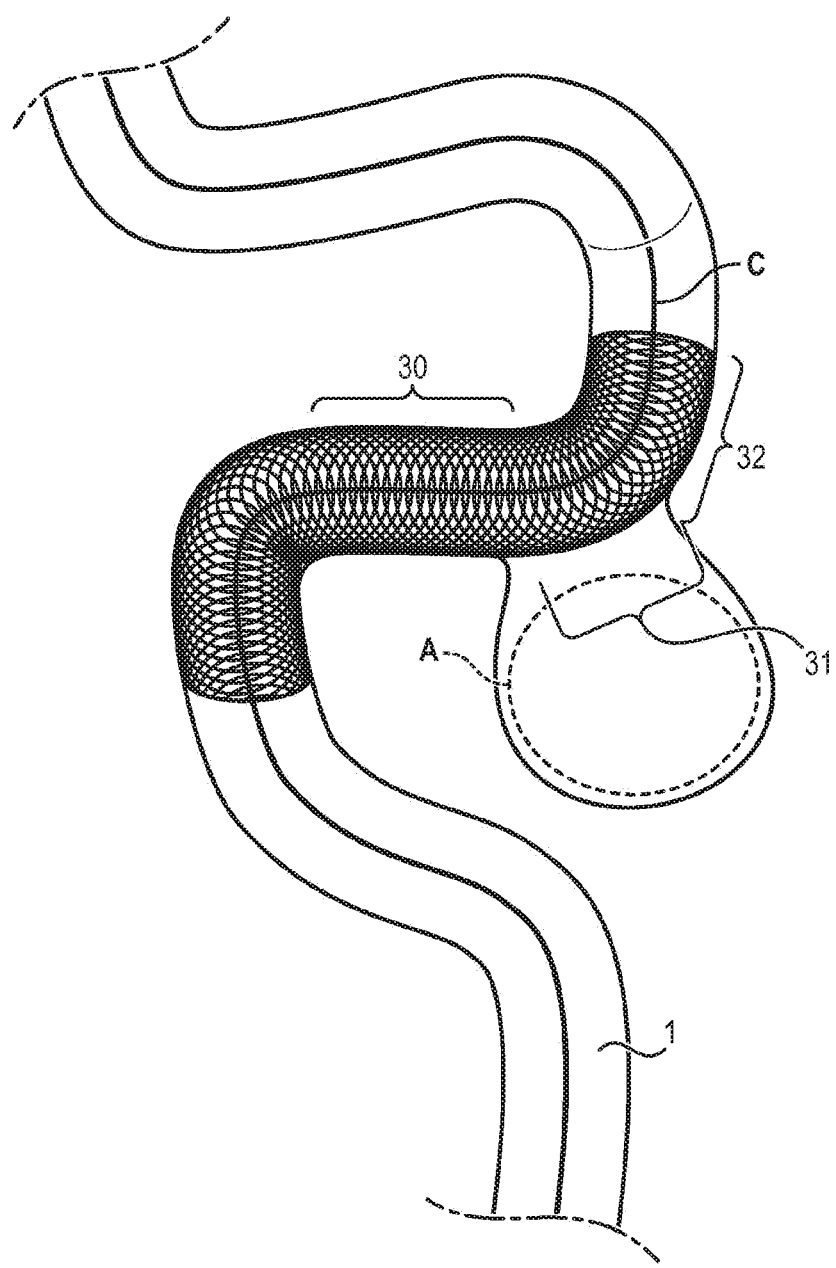

FIG. 3b correspond to a three-dimensional view of the same artery, in which the centreline of the artery is represented;

FIG. 3c corresponds to the same three-dimensional view in which an IMD of "flow diverter" type is represented;

FIG. 4a illustrates a sequence of steps of a method according to an embodiment, for determining the position of a "flow diverter" after deployment;

FIG. 4b illustrates a sequence of steps of a correction of geometric deployment, for determining the position of an IMD after deployment;

FIG. 4c illustrates a sequence of steps of a correction of mechanical deployment, for determining the position of an IMD after deployment;

FIGS. 5a, 5b, 5c and 5d schematically illustrate successive iterations within a step of simulation of the final position of a "flow diverter" taking account of geometric stresses;

FIG. 6 schematically illustrates transversal sections of an artery equipped with an IMD of "flow diverter" type, in several possible cases;

FIG. 7 illustrates a three-dimensional mapping of the degree of apposition provided for an IMD.

Figure 8A:
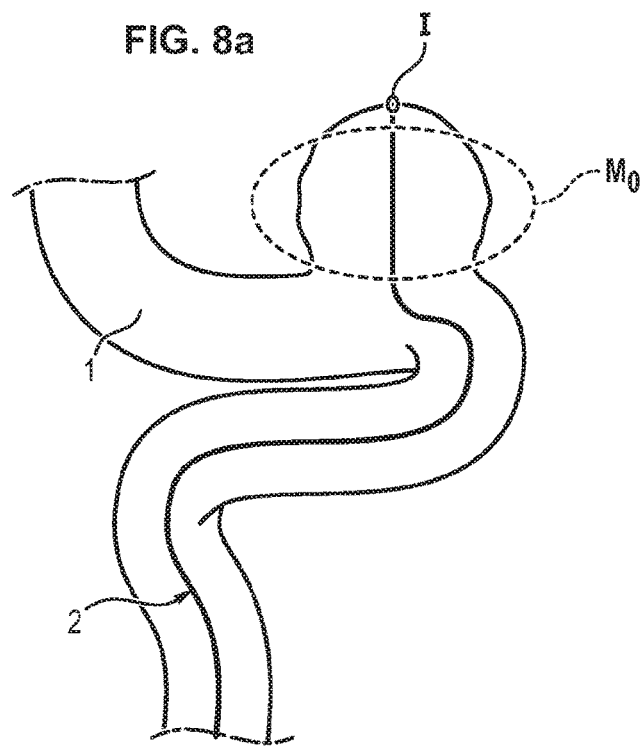
Figure 8B:
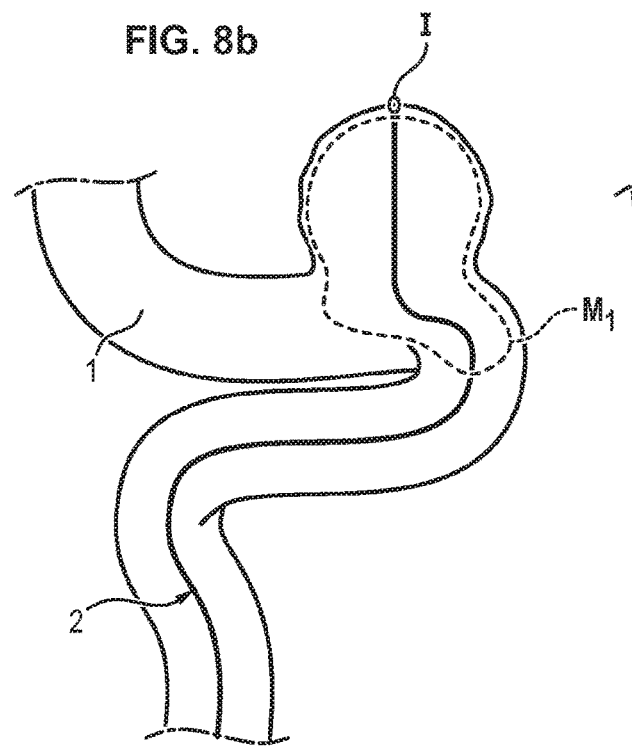
Figure 8C:
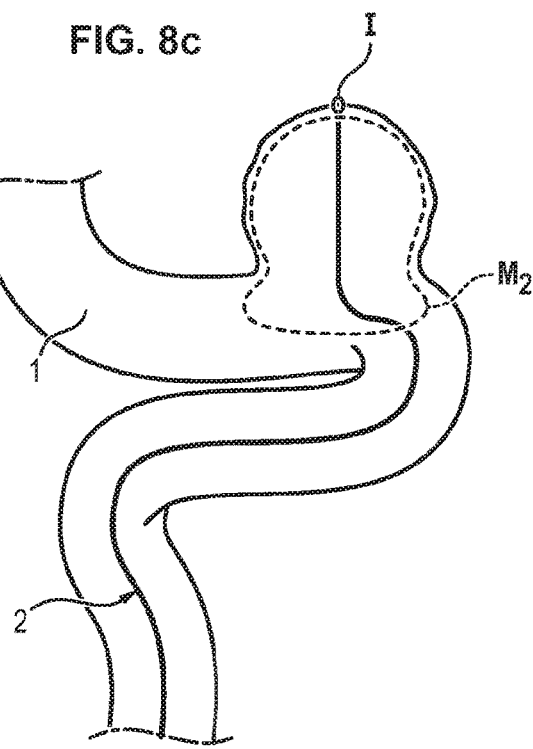

FIG. 8a illustrates the result of the step of positioning of the IMD in its initial position, FIG. 8b illustrates the result of the step of geometric simulation of the final position of the IMD and FIG. 8c illustrates the result of the step of simulation of a mechanical correction.

DETAILED DESCRIPTION OF EMBODIMENTS

The following description relates to the determination of the final position of an IMD within an artery. However, the invention may be used with the same advantages for any vascular structure of the human or animal body.

Hereafter, reference will indiscriminately be made to an "implant" or an "implantable medical device" (IMD) as being an expandable implant, being able to adopt a final position within an artery that is different from its initial position (before deployment), and which is also different from its rest position (deployment in free air) or "nominal position". "Morphological characteristics of the artery" is taken to mean a set of characteristics locally having an influence on the final position of the implant (notably but not restrictively the minimum diameter, perimeter, radius of curvature and spatial derivatives thereof). Furthermore, a region of interest, comprising the artery to treat, could be designated "ROI".

Furthermore, the description that follows specifically concerns a prothesis of "flow diverter" type, of substantially cylindrical or tubular shape. This implant is formed of a mesh made of material biocompatible with human tissue. It is maintained in a radially compressed and longitudinally lengthened position, for example in a catheter, before insertion. However, a method according to the invention may be applied with the same advantages for any type of expandable implant other than the "flow diverter", for example for an intraaneurysmal cage (intrasaccular device), for a device of conical shape, or instead a stent type device, for example a "laser-cut stent".

System for Determining the Positioning in Deployed Position of an IMD

Figure 1:
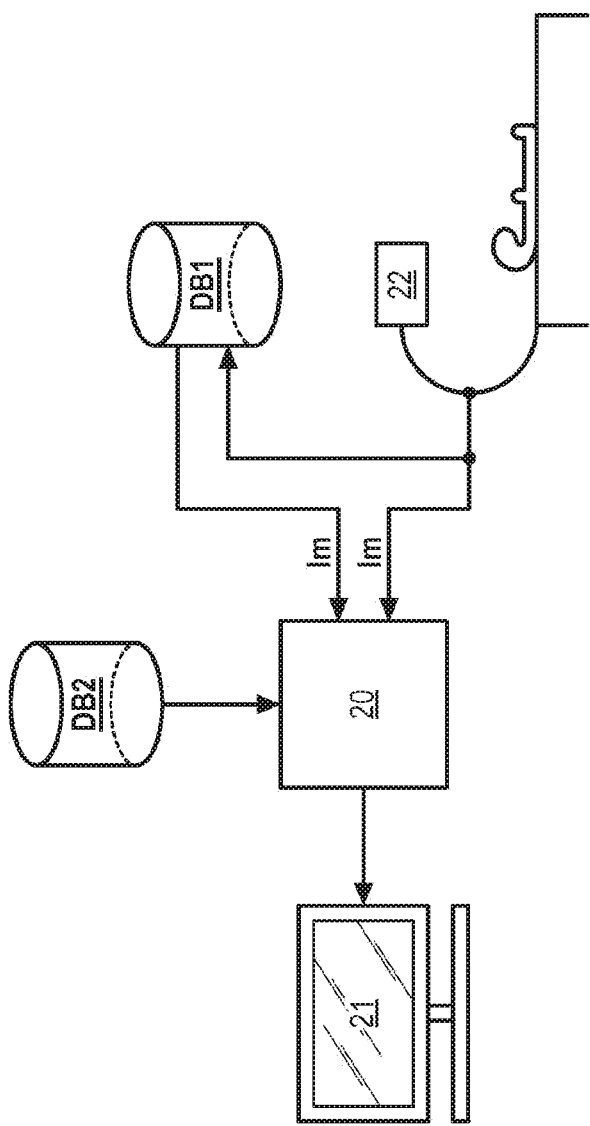
FIG. 1 illustrates a system able to execute a method according to the invention.

In FIG. 1 is represented a system for determining the positioning of an IMD comprising a processing unit 20 according to the invention. This processing unit is, for example, a processor configured to implement a method for determining the positioning of an IMD which will be described hereafter.

The processing means are, advantageously, configured to communicate with an acquisition unit 22, configured to acquire views making it possible to reconstitute a three-dimensional image of a region of interest of a patient, said region of interest comprising an artery, and/or to communicate with a database DB1 in which are recorded three-dimensional images acquired on a patient and/or views making it possible to reconstitute such three-dimensional images. The acquisition unit 22 may for example be an X-ray imaging system, and the views may for example be acquired within the scope of a neuro-radiology procedure such as for example the acquisition of a 3D angiography. The processing unit 20 communicates with the acquisition unit 22 and/or with the database DB1 so as to receive the images Im, by wired link and/or by wireless link by means of any suitable network (Internet network, etc). In an alternative, the processing unit may extract the images Im from a hard disc, or receive the images Im through a storage support playback device such as a CD reader or a USB port.

The processing means are further configured to communicate with a database DB2 comprising data concerning implantable medical devices, or IMDs. These data may for example be physical IMD characteristics, or pre-recorded IMD models. Said data may be supplied by IMD manufacturers, or determined analytically or experimentally. The link between the processing unit 20 and the database DB2 is achieved by any suitable means.

Finally, the processing unit 20 may communicate with a display device 21, supplying a graphic interface for displaying three-dimensional images of regions of interest and for any other display necessary for the implementation of the method that will be described hereafter. The display device 21 is associated with a user interface for the input of instructions and data.

Method for determining the positioning in deployed position of an IMD

Figure 2:
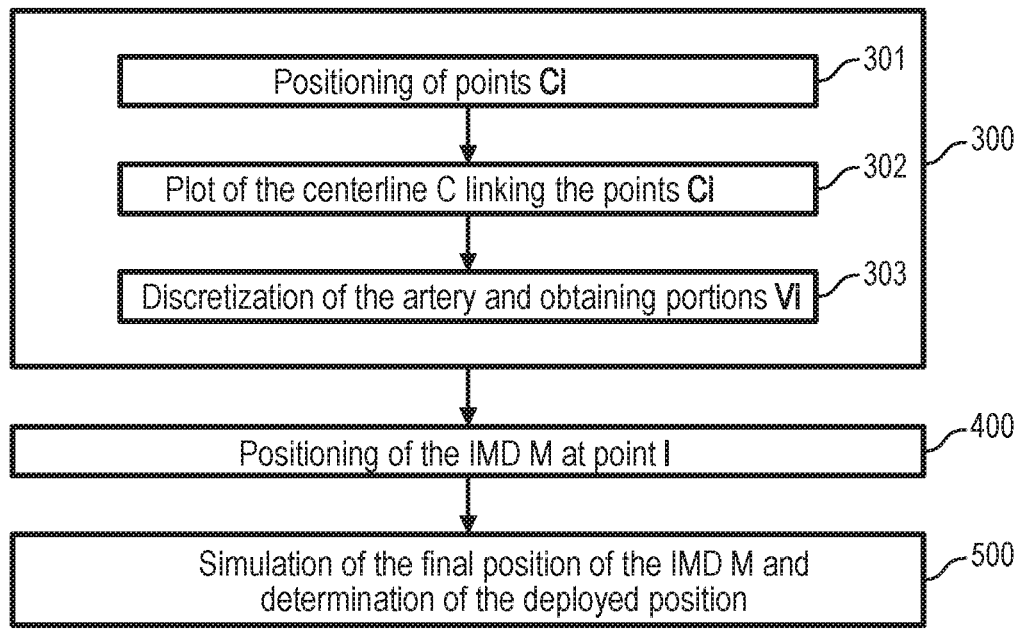
FIG. 2 illustrates a sequence of steps of a method for determining the final implant position according to the invention.

In FIG. 2 are represented the steps of a method 10, constituting an exemplary embodiment of a method of the invention for determining the deployed position of an extensible implant within an artery.

Hereafter, the body conduit treated by the insertion of an implant is an artery, and the implant is an endovascular implant; however, the invention could be used with the same advantages for a prothesis intended for the treatment of any other body conduit, in humans or animals.

In FIG. 3a is represented a two-dimensional view corresponding to an angiography of an artery 1 to treat, having in a zone A an aneurysmal sac.

This image is obtained, for example by a processing unit connected to an X-ray scanner or by any known means of same type.

Prior to the steps of the method 10, an initial positioning point D of the implant is determined, called for example "distal point" and, optionally, a second final positioning point P called for example "proximal point". These two points may, in the case of a flow diverter, correspond to the positions of the two ends desired by the clinician. An IMD reference is selected, automatically or manually by an operator, said reference corresponding to a type of implant with pre-recorded or manually selected dimensions. The method 10 may also provide an automatic selection of a suitable implant reference with suitable dimensions, as a function of information extracted from the three-dimensional image of the artery, and/or as a function of a distance between the proximal point and the distal point. Hereafter, it is considered that the selected implant reference corresponds to a "flow diverter". The method 10 furthermore takes as input a three-dimensional image Im of the artery. The protocol to obtain said three-dimensional image of the artery will not be detailed here.

The method 10 comprises a step 300 of determining a centreline C of the artery, at least at the level of the zone A. Indeed, to have access to the deployed position of the implant, it is advisable to determine the axis along which the implant may extend or retract within the artery. This axis globally corresponds to the centreline of the artery. The centreline C is determined at step 300 by placing the points $C_i$ at different longitudinal positions along the artery, within the internal volume of the three-dimensional image Im of the artery.

The points Ci are placed along the artery so as to obtain the most rapid path between an input point I in the artery, typically an input point of a micro-catheter to carry out the implantation of the IMD at the level of the region of interest, and an output point of the artery. The input and output points may be entered manually by an operator through the interface of the device 21, or may be determined automatically on the three-dimensional image of the artery.

"Most rapid path" is taken to mean minimisation of the travel time for blood between the point I and the output point.

Very advantageously, the placement of the points Ci from the point I is carried out by applying a gradient descent algorithm, to minimise the travel time along the points thus placed.

From a current point among the points Ci, the point following the centreline in the direction opposite to the gradient of the travel time function is sought.

The travel time function corresponds, for example, to a distance along a three-dimensional curve arc corresponding to the centreline, multiplied by a cost function having the dimension of the inverse of speed.

According to a particular embodiment represented in FIG. 2, step 300 comprises a sub-step 301 during which the processing unit successively calculates points $C_i$ along the artery. If the artery was perfectly cylindrical, the points $C_i$ would be placed successively along the axis of revolution of the cylinder then forming the artery. In reality, the artery is not locally cylindrical. The positioning of the points C, is thus carried out by seeking to minimise the distance between each point C, and the neighbouring surface of the artery. Moreover, the determination of a centreline point C, is also carried out by seeking to minimise the travel time of fluid along the centreline points already determined. The points $C_i$ may be obtained on consecutive portions $V_i$ considered in order.

At a sub-step 302, the centreline C linking the points C, is plotted on the three-dimensional image of the artery. Step 302 may comprise a calculation of an optimal path between the points C, determined previously, and the centreline then corresponds to said optimal path. The optimal path may be for example the most rapid path in the artery between the input of the micro-catheter within the artery (point I) and the output point of the artery (point S).

Finally, at step 303, the processing unit carries out the extraction, from the three-dimensional image of the artery, of three-dimensional portions $V_i$ of the artery, along the previously determined centreline. Advantageously, the portions extracted along the centreline correspond to sections of the artery, being able to have a tubular shape with circular section.

FIG. 3b is a view of a three-dimensional model for the artery 1 of FIG. 3a. In the view of FIG. 3b is represented the centreline 2 obtained for the artery 1 at the end of step 300. The initial point D of positioning an IMD is moreover marked. The view of FIG. 3b corresponds to a three-dimensional representation of the artery which may be supplied on the display device 21 during the execution of the method 10.

The method 10 next comprises a step 400 of insertion of an IMD M, corresponding to the implant reference taken at the start of the method. The distal end of the IMD M is placed at the initial point D (distal point), which is advantageously visible on the three-dimensional image. For example, the distal point D may be positioned on the periphery of the zone A to treat. The IMD M is placed around the centreline C determined at step 300. "Around" is taken to mean that the walls of the IMD M surround the centreline, even if the IMD is not necessarily centred on the centreline. If the IMD M corresponds to a "flow diverter", the IMD M may be taken as a tubular shape with its longitudinal axis coinciding with the centreline of the artery. The point D constitutes the distal end of the IMD M. The dimensions of the IMD M placed at the point D correspond to the dimensions of the implant at rest, which are not necessarily identical to the dimensions after deployment which will be determined in the remainder of the method.

These dimensions, specific to each reference of IMD M, may be selected automatically as a function of the positions of the point D and the proximal point, the distance between the centreline determined at step 300 and the walls of the artery, or as a function of the morphological characteristics of the artery, or instead manually. The reference of the IMD M may also be modified as a function of a first estimation of the apposition of the walls of the model M of IMD against the walls of the artery.

The initial position of the IMD M at the end of step 400 corresponds to a stress-free position, where the IMD is not stressed in the sense of a radial compression or a longitudinal compression by the walls surrounding the artery. At step 500, the position of the IMD M is corrected as a function of the morphological characteristics of the artery, so as to take into account the mechanical stresses exerted by the walls of the artery to obtain a final position after deployment. Advantageously, locally, the length and/or the diameter of the IMD M are corrected. Advantageously, the IMD M may be discretised into a set of connected segments in order to carry out the operation of simulation of the final position of the IMD M. Such a case will be detailed hereafter in relation to the method 40 of FIG. 4.

After simulation of the final position of the IMD M, the position obtained corresponds to the determined position of the IMD after deployment. Its extension may be spontaneous, or instead be caused during an operation of insertion of the implant. The final simulated position must thus enable an operator to note if the chosen implant reference and the initial size chosen are suited for the treatment of the artery. The operator may notably observe if the targeted vascular pathology is correctly treated, and if the implant after expansion would not produce undesirable secondary effects on other zones of a vascular tree visible on the three-dimensional image.

FIG. 3c reproduces the three-dimensional representation of FIG. 3b, in which the implant IMD M is represented after the implementation of step 500 for an implant reference of "flow diverter" type. FIG. 3c corresponds to a view supplied on a graphic interface connected to the processing unit. In the view of FIG. 3c may be discerned three implantation zones of the "flow diverter": a first zone where the implant adopts a globally tubular shape of slightly variable radius and a slightly deviated centreline 2, a second zone where the implant adopts a bent position, and a third zone where the implant once again adopts a globally tubular shape. The apposition of the implant is lower at the level of the saccular aneurysm collar represented here. On the other hand, the implant is correctly apposed on the wall of the artery opposite to the aneurysm. Although a representation of a degree of apposition of the implant is not provided in the view of FIG. 3c, such a representation could be provided here, for example according to the modalities that will be described hereafter in relation to the method 40.

In FIG. 4a are represented the steps of a method 40 for determining the position of a "flow diverter" type implant after expansion within an artery, according to a particular embodiment of the method of FIG. 2. Identical numerical references between the figures correspond to similar steps or to similar elements. This method may also be implemented by the processing unit 20 represented in FIG. 1.

In a step 100, a three-dimensional view Im of an artery to treat is acquired, for example by angiography. The three-dimensional image of the artery may be segmented by the "marching cubes" methodology known in the image reconstruction field. Reference could be made for the construction of three-dimensional images to the following publication: *Marching Cube: A high resolution* 3D *surface construction algorithm*, William E. Lorensen, Harvey E. Cline, Computer Graphics, 1987.

At step 200, a zone A is marked, manually by an operator or automatically, on the three-dimensional view obtained at the end of step 100. This zone A corresponds to an artery to treat by the insertion of an implant, and may notably correspond to a aneurysmal pathology of saccular or fusiform type, or any other type of aneurysmal pathology, or a localised shrinkage of the artery, or a stenosis, or a thrombosis.

At an optional step 250, the three-dimensional image Im is verified. It is notably possible to verify the quality of the image Im by thresholding: the three-dimensional image Im is superimposed on a two-dimensional radiography view under the same angle, to which a thresholding is applied. The three-dimensional image may be corrected as a function of the result of the comparison with the two-dimensional thresholded image, notably to verify the dimension of the arterial tree. The three-dimensional image Im may also be rescaled with respect to the two-dimensional radiography.

It should be noted that steps 100 to 250 are optional for the execution of the method 40. The method 40 could be executed by a processing unit receiving as input a three-dimensional image of the artery to treat with a zone A.

At step 300, a centreline C of the artery is determined by the processing means. The centreline thus obtained traverses the zone to treat. Very advantageously, the centreline may be determined according to the modalities described previously in relation to the method 10 of FIG. 2.

At an optional step (not represented in FIG. 2), from the three-dimensional image of the artery and the centreline determined at step 300, the processing unit may, if necessary, carry out a correction of an anastomosis not present on the real artery to treat, such as an artery-artery fusion or an artery-aneurysmal sac fusion. Such an error may occur during the reconstruction and may also be corrected by the operator.

At step 400, an IMD M corresponding to a preselected reference of "flow diverter" with dimensions at rest is positioned at an initial point D, in a manner similar to step 400 of the method 10. The IMD M is advantageously chosen of tubular shape with a constant radius section, along the centreline C determined at step 300 and centred on said centreline. The IMD M according to this initial positioning may extend beyond the walls of the artery in certain zones.

At step 410, the IMD M is discretised into a plurality of segments $M_j$, where the index j indexes the consecutive segments of the IMD M. Very advantageously, each of the segments $M_j$ of the discretised model is approximated by the processing means by a volume of cylindrical shape. If the IMD M obtained at the end of step 400 is tubular with constant radius section, all the segments $M_j$ correspond to tubes of same radius centred on the centreline C. The number of segments may be predetermined and independent of the morphological characteristics of the artery, and may for example be fixed at 200. The length of all the segments may be the same and be taken equal to the length of the centreline divided by the number of segments. In an alternative, the length of each of the segments may not be chosen uniformly. For example, the length of the segments may be chosen in such a way as to obtain a finer meshing on zones where the perimeter of the walls of the artery is highly variable, or instead on zones where the centreline is highly deviated. The discretisation of the IMD M may be carried out from the initial point D, and thus from one end of the initial position of the IMD M, up to the other end.

The model discretised into segments obtained at the end of step 410 is used to carry out a simulation of the final position of the IMD M. This simulation is done by taking into account stresses that are either geometric, or mechanical, or geometric and mechanical, exerted by the walls of the artery on the IMD M. An aim of taking into account these stresses is to obtain a simulated final position corresponding to a position of the implant after its expansion within the artery. Considering the simulation time of a mechanical correction in the general case, the fact of taking account uniquely initially geometric stresses exerted by the walls (without seeking a mechanical equilibrium at the level of the walls of the IMD) makes it possible to save computing time.

In relation with FIG. 4b, the step of simulation of the final position according to an embodiment 500 will be detailed here, in a first case where geometric stresses are taken into account.

At step 500, each segment $M_j$ is corrected in length and in diameter, while taking account of the variation in the intraarterial radius. As mentioned above, each segment may be approximated by a tubular volume. For each of these segments, a behavioural law of the IMD mechanically linking the length and the diameter is applied, said law being relative for example to the implant reference selected beforehand. This behavioural law may be linear or refined or non-linear, and may be determined experimentally, or be derived by prior analytical development, or instead be supplied in a database, for example if it is supplied by a manufacturer of the implant. The slope obtained for a refined approximation of the length as a function of the diameter may be negative, in the case where the implant, stretched longitudinally, retracts radially, and if compressed longitudinally, it widens radially.

Step 500 of correction of the position of the "flow diverter" IMD M may be implemented by iterations as follows.

Steps 501 and 502 are iterated one after the other for each of the segments $M_j$ in order.

At sub-step 501, the diameter of the segment $M_j$ is modified, from a current position of the segment $M_j$ stored in a memory of an accessible database of the processing unit. The modification of the diameter $D_j$ of the segment $M_j$ is carried out in such a way as to house the segment $M_j$ in the zone of minimum diameter of the portion of the artery surrounding the segment $M_j$, such that the walls of the segment $M_j$ touch said zone of minimum diameter. It is possible to take account of a maximum diameter of the segment $M_j$ given by a behavioural law; if the minimum diameter of the portion of the artery is greater than said maximum diameter, the diameter $D_j$ is then modified so as to be equal to said maximum diameter.

Next, at sub-step 502, the length $L_j$ of the segment $M_j$ is corrected, by means of the behavioural law of the IMD and the value of the diameter corrected at step 501 for the segment $M_j$. For example, if the segment $M_j$ is retracted radially during step 501, it is stretched at step 502.

These steps 501 and 502 are repeated for each of the segments, for an iteration of step 500.

At sub-step 503, the total length L of the IMD M is determined by summing the corrected lengths $L_j$ of the segments $M_j$.

At the end of the determination of the geometric position, it may be necessary to correct the position of the IMD if the mechanical equilibrium is not sufficiently satisfactory by starting from the final known position of the IMD, either the position resulting from step 400, or the position resulting from step 500. The processing unit may implement a simulation of final position of the IMD M according to a second alternative, where a mechanical equilibrium is sought for the simulated walls of the IMD M. This second modality corresponds to the embodiment 800 for the step of simulation of the final position of the IMD M.

Sub-steps of this embodiment are detailed in FIG. 4c.

At sub-step 801, a mechanical modelling of the IMD is proposed, based for example on the finite elements method which takes account of the mechanical links between the different segments of the IMD, in its configuration free of mechanical stresses.

At sub-step 802, from the stress free state read in a database BD2, the segments $M_j$ in the last known position are transformed. For each segment $M_j$, a geometric transformation is applied between the configuration free of mechanical stresses (position at rest of the IMD) and the starting configuration of the mechanical correction:

either from step 400 of positioning of the IMD according to the initial position, or from step 500 of geometric simulation of the final position of the IMD.

At sub-step 803, for each segment $M_j$, a mechanical modelling of the contact with the surface of the artery 1 is defined by the processing unit.

Finally, at sub-step 804, a non-linear calculation of the mechanical equilibrium for the walls of the IMD M is carried out, a correction of the position of the segments $M_j$ of the IMD being able to be applied if necessary. The final simulated position reached corresponds to a position where the walls of the IMD are at the mechanical equilibrium thus calculated.

FIG. 5a schematically illustrates in the example of an artery 1 the modification of diameter and length of the segments $M_j$, with an index j ranging from 1 to n=6, during a first iteration of steps 501 to 503. In this figure, the positions of the segments $M_j$ before correction are in solid lines, and the corrected positions $M'_j$ are in broken lines. It may be observed that the segments of length and diameter corrected to take account of the morphological characteristics of the artery are no longer necessarily connected to each other.

Next, the length obtained at step 503 for the IMD is compared at sub-step 504 with the length obtained at the preceding iteration of steps 501 to 503. If the difference in total length L obtained is sufficiently close to zero (convergence criterion: absolute value of the difference between said lengths), then the iteration loop is exited, and the lengths $L_j$ of the segments are determined as being the lengths of the segments of the implant of which the final position has been simulated. For example, the absolute value of the difference is compared with a predetermined threshold.

If, on the other hand, the total length L is not determined as sufficiently close to the preceding total length, then a new iteration of steps 501 to 503 is implemented. To prepare this new iteration while taking account of the modifications made to the lengths and diameters of the segments, the position of the segments is adjusted such that they are again connected, for example from the initial point D. This is visible in FIG. 5b, corresponding to the same example as that of FIG. 5a for the following iteration of steps 501 to 503. The solid line corresponds to the position of the segments before the implementation of sub-steps 501 and 502 for said iteration: it is noted that the lengths and diameters of the segments indeed correspond to the corrected positions of FIG. 5a, and that the segments $M_j$ have been repositioned one following the other. The fact of having repositioned the segments one following the other may create once again non-correspondences between the diameter of the segments and the walls surrounding the artery 1, and give rise to a new re-dimensioning of the segments.

In this respect, in FIGS. 5c and 5d are represented the two iterations consecutive to those of FIGS. 5a and 5b, for the same segments. At the end of the iteration represented in FIG. 5d, the final length L of the implant is determined as corresponding to the sum of the lengths of the segments.

On exiting the loop of step 500, the segments are repositioned one following the other, and the simulated position of the IMD M after expansion of the implant is obtained. The final length of the implant once deployed is thus taken equal to the sum of the lengths $L_j$ of the segments in this simulated position.

The discretisation method described above in relation with steps 400 to 500 is applicable to any type of pathology of the artery. It makes it possible to have a prediction of the final length of the implant after expansion which is very close to reality, and thus to guide the choice of the clinician. The discretisation proposed here is advantageous, in that the corrected lengths of each of the segments of the model at a given iteration are taken into account for the following iteration.

According to an alternative embodiment of the method 40, the correction of position of the IMD M at step 500 takes account not only of the morphological characteristics of the artery, such as the perimeter of the artery in the vicinity of a segment, but also the level of push-pull applied by the practitioner during the insertion of the implant. Indeed, if a certain stress is exerted on the implant during the insertion, for example in the sense of a longitudinal compression generating a radial extension, the implant may locally adopt a perimeter which exceeds the circumference of the circle inscribed in the walls of the artery. The implant may adopt a locally non-tubular shape (with non-circular radial sections). Notably, a stress in the longitudinal sense may be exerted voluntarily during the placement of the implant, to extend radially the implant and force its apposition against the walls of the artery, for example in a zone where said walls do not have a circular section.

For example, being a "flow diverter" segment the corrected diameter of a segment may be determined as a function of the perimeter surrounding the walls of the artery, which may tend to compress the segment radially, by also taking into account the longitudinal compression exerted during the implantation which may tend to extend the segment radially. To take into account the level of push-pull, the calculation of the corrected diameter of a segment $M_j$ at step 501 may be carried out by allocating a weighting for the influence of the perimeter surrounding the artery.

It will easily be understood that the other modalities described hereabove for the implementation of step 500 remain applicable in this case.

The impact of the level of push-pull for the simulation of position after expansion of the implant is illustrated in the schematic views of FIG. 6. On a non-circular section of the walls of an artery 1, a "flow diverter" IMD M having a stress free cylindrical shape is represented.

In the top view of FIG. 6, it may be observed that the selected IMD M has a radius at rest too small to be apposed correctly against the walls of the artery 1.

For the same implant visible in the view in the middle of FIG. 6, corresponding to an absence of longitudinal compression, the IMD M is extended radially, with the result that its diameter reaches approximatively the minimum diameter of the walls of the artery 1 on the section represented. However, the artery not being locally circular, zones remain of the artery for which the walls of the implant model are not correctly apposed on the walls of the artery 1.

Finally and for the same implant visible in the bottom view of FIG. 6, with an important longitudinal compression, the radial expansion of the walls of the IMD M is sufficient to obtain total apposition of the implant against the walls of the artery, by here making the hypothesis of a perfectly rigid artery. Furthermore, the longitudinal compression is sufficient to impose on the implant a locally non-circular shape after expansion. In reality, the surface of the artery is not rigid, and the radial force applied by the walls of the implant in the case of a non-zero longitudinal compression may generate deformations both of the walls of the implant and the surface of the artery.

The application of a "push/pull" during the insertion of the implant thus makes it possible, for an implant of "flow diverter" type, to obtain good apposition of the implant against the walls of the artery, notably on zones where the artery is locally non-circular. The alternative of step 500 described above makes it possible to take account of the possibility of applying a "push/pull", and thus makes it possible to make the simulation of the implant reliable.

Optionally and advantageously, at the end of the determination of the corrected position of the IMD M corresponding to the simulated position of the implant, an additional step 600 of determining the degree of apposition of the implant is implemented, as represented in FIG. 4*a*.

Once the position of the implant IMD M after expansion has been simulated, the processing unit may calculate the degree of apposition as being the proportion of the surface of the implant on which the walls of the implant have good apposition against the walls of the artery. For example, for the cases described previously in relation to FIG. 6, the top view corresponds to a degree of apposition of 0% and the bottom view corresponds to a degree of apposition of 100%. It will easily be understood that, in the case of an aneurysmal sac type pathology, and for an implant of "flow diverter" type, it is not desired to obtain good apposition of the walls of the implant against the walls of the aneurysmal sac; on the other hand, it is desirable to obtain good apposition of the device against the other zones of the artery.

In the case of an IMD which could not be a "flow diverter", such as for example an intraaneurysmal cage, the apposition could be determined by considering the mechanical contact force imposed by the wall of the artery on the walls of the implant, or instead by considering the distances between nodes of the walls of the IMD and the neighbouring walls of the artery (the IMD being considered as correctly apposed below a certain distance threshold).

Optionally, the method 40 may comprise an additional step 700 of determining the porosity of the walls of the IMD M. This step could alternatively be implemented before step 600 of determining the degree of apposition of the walls of the IMD. The determination of the porosity of the walls of the IMD M is done according to any known method of the prior art.

At the end of the determination of the degree of apposition for the IMD M, independently of the implementation of step 700 of determining the porosity of the walls of the IMD, the processing unit may display, via the display device 21, a three-dimensional view of the artery treated with the simulated three-dimensional position of the implant, and to further display a mapping of the degree of apposition over the whole surface of the implant. Such a view is represented schematically in FIG. 7, in which may be seen an artery 1 treated with a "flow diverter" at the level of a zone A along a centreline C. For the zones 30 and 32, the apposition of the implant against the walls of the artery 1 is more important than at the level of the collar of the aneurysm, on the zone 31.

At the end of an iteration of the method 40 for determining the positioning in deployed position of the IMD, if the final position determined is insufficiently close to the walls of the artery (for example, if the final apposition is considered insufficient), it is possible to provide a new IMD model so as to better approach the walls of the artery. It is possible to take account of a maximum diameter of the segments $M_j$ given by a behavioural law; if the minimum diameter of the portion of the artery is greater than said maximum diameter, the diameter $D_j$ is then modified so as to be equal to said maximum diameter.

In an alternative, steps 400 and 500 such as described above may be reiterated with a different implant reference, having for example a different nominal diameter. The comparison of several final positions of IMD obtained for different implant references, by potentially varying the positioning of the distal point D and/or the proximal point P, allows the clinician to select the implant reference and the modalities of intervention the most suited to the treatment of the pathology that the artery has.

FIG. 8a illustrates the result of the step of positioning the IMD in its initial position, for an IMD of intraaneurysmal cage type. At the end of step 400, an implant of this type has been positioned in the three-dimensional image of the artery 1, according to an initial position $M_0$, along the centreline 2 calculated for example according to step 300 described previously.

FIG. 8b represents the visible result on the graphic interface at the end of an iteration of step 500 of simulation of final position of the IMD, while taking into account uniquely the geometric stresses exerted by the intrasaccular walls. A position $M_1$ of the IMD is thus obtained.

Finally, in FIG. 8c, the result visible on the graphic interface is represented, at the end of an iteration of step 800 of simulation of the final position of the IMD taking account of mechanical stresses exerted by the walls, by seeking to resolve the mechanical equilibrium for the walls of the IMD according to the position $M_1$ determined previously.

For this example, much more computing time would have been required to calculate the mechanical equilibrium according to step 800 from the initial position $M_0$, compared to the computing time required here to compute the position $M_2$ from the position $M_1$ for which the geometric stresses exerted by the intrasaccular walls have already been taken into account.

The invention claimed is:

1. Method for determining the positioning in deployed position of an expandable implantable medical device, or IMD, said medical device being intended to be deployed in a vascular structure (1), the method comprising, on the basis of a three-dimensional image of a region of interest comprising the vascular structure in which a positioning point (D) of the IMD has been defined, the following steps:
   determination (300) of a centreline (C) of the artery,
   positioning (400) of the IMD (M) according to an initial position, around the centreline (C),
   simulation (500, 800) of the final position (M) of the IMD after deployment, as a function of the stresses exerted by the walls of the vascular structure (1) on the IMD, wherein the determination (300) of the centreline (C) comprises placing points at different longitudinal positions along the vascular structure, so as to minimise a travel time of fluid along said points (Ci) between an input point (I) in the vascular structure and an output point (S) in the vascular structure,
   said points forming the centreline (C), and
   wherein the simulation of the final position of the IMD is carried out as a function of a level of longitudinal push-pull intended to be applied to the IMD during its implantation.

2. Method according to claim 1, wherein the determination (300) of the centreline (C) comprises sub-steps consisting in:
   plotting (302) the centreline (C) passing through said points (Ci);
   discretising (303) the vascular structure so as to obtain a succession of three-dimensional portions of the vascular structure along the centreline.

3. Method according to claim 1, wherein the step of positioning the IMD according to the initial position is followed by a step of discretisation of the IMD into a set of longitudinal three-dimensional segments, the step of simulation of the final position (500) taking into account the geometric stresses exerted by the walls of the vascular structure on the IMD, by the following sub-steps:
   a) for each segment ($M_a$), modification (501) of the diameter of said segment as a function of the perimeter of the vascular structure in the vicinity of said segment, and modification (502) of the length of said segment, by means of a behavioural law of the IMD linking said length to said diameter of the segment,
   b) calculation (503) of a length of the IMD as being the sum of the lengths of the segments at the end of step a),
   c) comparison (504) of the two final lengths calculated at step b), wherein
   if the absolute value of the difference between the two calculated final lengths of IMD is below a threshold, the length of the IMD in final position is the final length calculated at step b) and
   if said absolute value of the difference is above said threshold, the correction step comprises a step of adjustment of the position of each segment of the IMD while taking account of the modifications of length of the segments at the end of step a), and a repetition of steps a) to c) with the segments thus modified.

4. Method according to claim 1, comprising a step of determination of a degree of apposition of the IMD on the walls of the vascular structure, in final position.

5. Method according to one claim 1, wherein the step of simulation of the final position (800) takes into account the mechanical stresses exerted by the walls of the vascular structure on the IMD, by the following sub-steps:
   allocation (801) of a mechanical modelling to each segment ($M_a$),
   for each segment ($M_j$), transformation (802) of the diameter ($D_j$) of said segment, and allocation of a mechanical contact between said segment ($M_j$) and the vascular structure (1),
   resolution (803) of the mechanical equilibrium of the IMD to obtain a final position of the IMD.

6. Method according to claim 1, comprising a preliminary step (250) of verification of the 3D reconstruction of the surface of the vascular structure in the region of interest, said verification being carried out by thresholding.

7. Method according to claim 1, comprising, after the step of determination (300) of the centreline a step of correction of one or more non-physiological anastomoses of said surface, such as an artery-artery fusion or an artery-aneurysmal sac fusion.

8. Method according to claim 1, comprising an additional step of three-dimensional graphic representation of the vascular structure in the region of interest, comprising the determined centreline (C), as well as optionally a degree of apposition.

9. Method according to claim 1, wherein the IMD is of flow diverter, or intra-aneurysmal cage, or stent laser-cut type.

10. Method according to claim 1, comprising a step (700) of determination of a porosity of the walls of the IMD in final position.

11. Computer programme product comprising code instructions for the execution of the method according to claim 1, when it is executed by processing means of a processing unit.

12. Processing unit (20) configured to obtain a three-dimensional vascular structure image acquired from an acquisition unit (22), and further configured to simulate a final position of an expandable IMD, by the implementation of the method according to claim 1.

13. Method according to claim 1, wherein the travel time between the placed points (Ci) is minimised using a gradient descent algorithm, said points forming the centreline (C).

14. Method according to claim 4, wherein, if the final position determined for the IMD is insufficiently close to the walls of the vascular structure, the step of simulation (500) of the final position is reiterated with segments ($M_j$) of larger diameters, so as to bring closer together the segments of the walls of the vascular structure.

15. Method according to claim 4, wherein the behavioural law is a relationship dependent on the geometric and mechanical parameters of the IMD.

* * * * *